United States Patent
Rauth et al.

(10) Patent No.: US 6,822,081 B2
(45) Date of Patent: Nov. 23, 2004

(54) PROCESS FOR THE ISOLATION AND/OR PURIFICATION OF A PROTEINACEOUS MATERIAL

(75) Inventors: Holger Rauth, Berlin (DE); Richard Reinhardt, Berlin (DE); Eckhard Nordhoff, Berlin (DE); Markus Kalkum, New York, NY (US)

(73) Assignee: Max-Planck Gesellschaft zur Förderung der Wissenschaften e.V., München (DE)

( * ) Notice: Subject to any disclaimer, the term of this patent is extended or adjusted under 35 U.S.C. 154(b) by 86 days.

(21) Appl. No.: 09/760,379

(22) Filed: Jan. 16, 2001

(65) Prior Publication Data

US 2001/0034017 A1 Oct. 25, 2001

Related U.S. Application Data

(60) Provisional application No. 60/175,958, filed on Jan. 13, 2000.

(51) Int. Cl.[7] .......................... C12Q 1/00; C07K 14/00; G01N 33/68
(52) U.S. Cl. ....................... 530/415; 530/412; 530/417; 530/350; 435/4; 427/132
(58) Field of Search ................................. 530/350, 412, 530/415, 417; 427/132, 2.22, 128, 131, 222; 435/4

(56) References Cited

U.S. PATENT DOCUMENTS 5,283,079 A * 2/1994 Wang et al. .................... 427/2
6,005,082 A * 12/1999 Smeds ......................... 530/417

FOREIGN PATENT DOCUMENTS

WO      WO 98/12717    * 3/1998

OTHER PUBLICATIONS

Guo et al., Disi Junyi Daxue Xuebao 20(1), 85–88 (1999).*
Margel et al., Analytical Biochemistry 128, 342–350 (1983).*
Kato et al., Resin–Based Support for Reversed–Phase Chromatography of Proteins. J. Chromatography 333, 93–106 (1985).*
Pearson et al., The Importance of Silica Type for Reverse–Phase Protein Separations. In High Performance Liquid Chromatography of Proteins and Peptides (edited by Hearn et al.) pp. 81–93 (1983).*
Belew et al., Purification of recombinant human granulocyte–macrophage colony–stimulating factor from the inclusion bodies produced by transformed *Escherichia coli* cells. J. Chromatography A, 679 (1994) 67–83.*
Pharmacia Biotech (1997) pp. 231 and 233.*

* cited by examiner

*Primary Examiner*—Jon P. Weber
*Assistant Examiner*—Chih-Min Kam
(74) *Attorney, Agent, or Firm*—Rothwell, Figg, Ernst & Manbeck, P.C.

(57) ABSTRACT

The invention relates to a process for the isolation and/or purification of a proteinaceous material, wherein a solid phase comprising a mixture of hydrophobic and hydrophilic groups is used.

9 Claims, No Drawings

PROCESS FOR THE ISOLATION AND/OR PURIFICATION OF A PROTEINACEOUS MATERIAL

This application claims the benefit of U.S. Provisional Application No. 60/60/175,958, filed Jan. 13, 2000.

The invention relates to a process for the isolation and/or purification of a proteinaceous material, wherein a solid phase comprising a mixture of hydrophobic and hydrophilic groups is used.

For many applications proteinaceous material is required to be in an isolated or purified form, in particular, to be free of interfering contaminations. Therefore, proteins obtained by conventional processes must be purified prior to the desired application in most cases. For example, sequencing of proteins requires products being free of contaminations which might interfere with the sequencing reaction. For a qualitative or quantitative determination of proteins the sample must also be free of contaminations which might interfere with the detection method. Using UV-spectroscopy the sample must be purified from constituents having an absorption in the same wavelength range as the analyte. Mass-spectrometric analysis of proteins, e.g. with MALDI-MS (Matrix-Assisted Laser Desorption/Ionization-Mass Spectrometry) also requires a sample preparation which provides the analyte essentially free of any other sample components which might interfere with analysis.

If only a few samples per day are to be processed, purification can be done manually, e.g. using conventional columns. However, if numerous samples have to be purified, a purification process is highly recommendable which is technically easy to perform in order to minimize personnel, money and time expenses. The process therefore desirably is easy to automate, fast and cost-efficient.

So far, several processes for the purification of proteins are known. Commonly used reversed phase chromatography is based on unspecific reversible binding of proteins and peptides to hydrophobic groups, being located and fixed to a support material within a column. For packing a column suitably for column-chromatographic purification of proteins organic solvents are usually employed to prevent the column fill material (stationary phase) from sticking together, since in an aqueous solution agglutination of the stationary phase material occurs because of its hydrophobic surfaces. However proteins are often present in aqueous solutions or samples. Binding of the proteins to the fixed stationary phase usually takes place in an aqueous solution, whereas for elution from the solid phase an organic solvent is added. Due to the hydrophobic character of the stationary phase, individually mobile solid phase particles cannot be used in an aqueous solution, since the solid phase particles would agglutinate. Thus a direct contact of a sample, such as urine or blood, with a conventional binding phase material in loose form is not feasible. Further, since conventional binding phase particles can be used only packed in a column, a combination of reversed phase purification with other separation technologies such as magnetic particle technology cannot be successfully performed. A further drawback of column-chromatographic purification processes is that they are rather complex and expensive and are difficult to automate.

Therefore, it was an object of the invention to provide a process for the isolation or purification of proteins, which overcomes the above-mentioned drawbacks of the known processes at least partly and which, in particular, provides easy and cost-efficient purification of a large number of samples.

The invention provides a process for the isolation and/or purification of a proteinaceous material comprising the steps:

(a) providing an aqueous sample comprising a proteinaceous material, (b) contacting the aqueous sample with a solid phase comprising a mixture of hydrophobic groups and hydrophilic groups on at least one surface thereof, wherein said proteinaceous material binds to said at least one surface and (c) separating off other sample components.

The process according to the invention allows for isolation, purification and/or concentration of proteinaceous material from aqueous samples. The proteinaceous material may be dissolved or dispersed in the aqeous sample, solutions being preferred. The proteinaceous material preferably is selected from peptides, proteins and any material which comprises at least partly peptidic bonds. Also comprised by the term proteinaceous material, as used herein, are adducts of peptides and/or proteins with other molecules, for example, sugars, lipids, nucleic acids and the like.

The solid phase used in the process according to the invention comprises a mixture of hydrophobic groups and hydrophilic groups. The hydrophobic groups serve to bind the proteinaceous material. The proteinaceous material is preferably bound reversibly and unspecifically to the hydrophobic groups located on at least one surface of the solid phase, Binding is, thus, not limited by specific binding pairs having high affinity such as streptavidin/avidin. In addition to the hydrophobic groups which are capable of binding proteinaceous material the solid phase used according to the invention comprises hydrophilic groups on at least one surface thereof, which hydrophilic groups prevent the solid phase from sticking together in an aqeous environment. By adding hydrophilic groups in adequate proportions the characteristics of the solid phase coated with hydrophobic groups can be varied. The configuration and numerical proportion of hydrophilic and hydrophobic groups are calculated in such a way that reversed phase binding of proteinaceous material, in particular, of peptides and proteins, will still take place, but no agglutination of the particles in an aqeous environment is observed. The choice of the functional hydrophilic and hydrophobic groups as well as the amount thereof can be individually adjusted for the respective analyte and the type and size of solid phase used.

Surprisingly, it was found that proteinaceous material can be bound to the solid phase used according to the invention with high yield, thus reducing the amount of solid phase required for purification.

Preferably, the solid phase comprises solid particles. Due to the addition of hydrophilic groups agglutination of small particles having hydrophobic groups located on their surface can be prevented according to the invention. Therefore, small individually mobile particles can be used in an aqueous solution without the necessity to pack them or to fix them on a support material. The solid phase preferably comprises solid particles having a diameter from at least 1 nm up to 10 nm. More preferred nanoparticles are used having a diameter of preferably at least 1 nm, in particular, at least 5 nm and, most preferred, at least 10 nm and up to 1.000 nm, preferably up to 500 nm, most preferably up to 100 nm and/or microparticles having a diameter of at least 1 μm, preferably at least 5 μm and up to 1.000 μm, preferably up to 500 μm.

Basically, however, any solid phase known to the skilled person may be used as solid phase such as microtiter plates, vessels such as Eppendorf vessels, Greiner tubes, Nunc tubes and the like. Preferably, solid particles having a diameter $\geq 1$ nm to $\leq 1$ mm are used as solid phase, thus providing a favorable specific surface per g of particle.

The method of the invention allows the use of most different solid phase materials. Silica, a plastic material such as polystyrene or a magnetic or magnetizable material is used preferably as solid phase material and, in particular, gamma-iron oxide. If a magnetic solid phase is used, further advantages can be achieved. In particular, it is possible this way to combine reversed phase purification of proteinaceous material and magnetic particle technology. Magnetic separation can be performed relatively easily and is easy to automate. Moreover, if paramagnetic or para- and ferromagnetic particles are used as solid phase, sticking together of the solid particles can be further reduced. Usually small magnetic particles having a diameter within nm or μm range are used in magnetic particle technology (e.g. by the company Dynal, Oslo, Norway), in the case of which the problem of sticking together is especially severe. The purification of the invention, however, can be performed without the solid phase particles sticking together, since the hyrophobic groups required for binding are supported by a sufficient number of hydrophilic groups. Thus, proteinaceous material, in particular, peptides or proteins, can be isolated from an aqeous solution using magnetic beads.

The part of the solid phase used which is contacted with the solution preferably contains $\geq 1\%$, in particular, $\geq 5\%$, preferably $\geq 10\%$ and up to $\leq 90\%$, especially $\leq 50\%$ and preferably $\leq 30\%$ hydrophobic groups on the surface. The amount of hydrophilic groups is preferably $\geq 1\%$, especially $\geq 5\%$, preferably $\geq 10\%$ and up to $\leq 90\%$, especially $\leq 50\%$ and preferably $\leq 30\%$. The ratio of hydrophobic to hydrophilic groups, on a molar basis, is from 1:100 to 100:1, especially from 1:10 to 10:1. The ratio of hydrophobic and hydrophilic groups to be used each for a particular analyte and a particular type and size of solid phase can be readily determined by a skilled artisan who will take into account that from a certain amount of hydrophobic surface groups which can be easily determined by a him for the respective solid phase, solid phase particles stick together in aqueous solution, as a result of which the solid phase can no longer be resuspended. In that case the amount of hydrophilic groups has to be increased accordingly.

According to the invention preferably small particles (diameter $\geq 1$ nm to $\leq 100$ μm), in particular, magnetic particles are used carrying functional hydrophobic groups on their surface, to which the proteinaceous material can be bound unspecifically and reversibly, as well as hydrophilic groups. Advantageously, hydrophobic functional groups known from the reversed phase chromatography are used, since their immobilization and handling is well-known to a skilled artisan.

The hydrophobic and hydrophilic groups can be present mixed on the solid phase on a molecular size scale. However, it is also possible to use a solid phase with several active surface areas containing hydrophobic groups separated from each other, for example, by inert regions. In this way it is possible to provide several spatially separated fields having different functionalities.

The hydrophobic and hydrophilic groups, respectively, on the surface of the solid phase can be part of the solid phase material used or can be prepared, for example, by derivatization of the solid phase material or by coating. Applying the functional hydrophobic and hydrophilic groups, respectively, by coating or coupling has the advantage that the basic material of the solid phase can be chosen freely.

The hydrophobic groups arranged on the surface are preferably organic hydrocarbon-containing groups and can have cyclic, linear or/and branched structures. The hydrophobic groups are selected preferably from $C_1$–$C_{30}$ alkyl groups or/and $C_5$–$C_{30}$ aryl groups, preferably from $C_8$–$C_{24}$ alkyl groups and, especially preferred from $C_8$, $C_{18}$ alkyl and mixtures thereof, with octadecyl ligands being most preferred.

Besides hydrophobic groups the solid phase used according to the invention also has hydrophilic groups, in particular, hydroxyl and/or oxide groups. Such hydrophilic groups can be part of the solid phase material or can be prepared, e.g. by derivatization of the solid phase material or can be applied by coating the solid phase material. It is also possible to provide the hydrophilic groups by means of one of the pre- or intermediate coatings mentioned below The hydrophilic groups prevent the solid phase from sticking Together in an aqueous environment. The hydroxyl groups can comprise inorganic hydroxyl groups, e.g. silicic acid groups, and/or organic hydroxyl groups, e.g. mono- or polysaccharides such as agarose. Further suitable hydrophilic groups comprise carbonyl, carboxyl, ester, amino, thiol, sulfate, sulfonyl and similar groups and combinations of such groups. Polyol derivatives such as polyalkylene glycol derivatives can be used as hydrophilic groups as well.

The arrangment and the ratio of hydrophobic and hydrophilic groups on the surface of the solid phase intended for binding the proteinaceous material is such that the respective particles just do no longer stick together in aqeous solution, however, the binding of the proteinaceous material still takes place effectively. The functional groups as well as their arrangement can be adapted by skilled artisan to the respective parameters such as particle size, particle density, analyte, particle material, sample environment etc. It is possible, for example, to apply the hydrophilic groups regions or in microregions separated from hydrophobic groups. However, a mixed surface wherein the hydrophobic and hydrophilic groups coexist is preferred. The hydrophilic groups can also be introduced by suitably substituted organic molecules, e.g. hydroxy-substituted alkyls An example of a preferred mixed surface is an alkyl/OH surface, especially a $C_{18}$-alkyl/$C_8$-alkyl/OH surface or a $C_{18}$-alkyl/OH surface.

The hydrophobic and hydrophilic groups, respectively, can be applied to the solid phase directly or via a pre- or intermediate coating. Suitable pre-coatings, for example, are a polysilicic acid matrix or/and a monosaccharide matrix.

These pre-coatings provide hydrophilic groups. Other suitable pre-coatings are partners of a specific binding pair, e.g. streptavidin/avidin, to which the actual functional groups are then applied.

Binding of the hydrophobic and hydrophilic groups, respectively, to the solid phase and the pre-coating, respectively as well as binding of the pre-coating to the solid phase can take place covalently, e.g. by esterification, or adsorptively by high affinity interactions. In an especially preferred embodiment a precoating consisting of polysilicic acid and monosaccharide is applied on a solid phase e.g., gamma-iron oxide particles having a diameter in nm or $\mu$m range ($\geq 1$ nm to $\leq 100, \mu$m). This precoating is then provided with hydrophobic groups, especially alkyl groups and with hydrophilic groups, especially hydroxyl groups.

The preferred use of magnetic particles allows to separate the solid phase, to which the proteinaceous material is bound, from other sample components by magnetic means, so that the whole procedure or one or several steps thereof is easy to automate.

An aqueous sample containing a proteinaceous material can be used directly for the process of the invention. Suitable samples for example, comprise urine, blood, serum or other aqueous liquids. The aqueous sample preferably comprises at least 10 vol.-%, preferably at least 50 vol.-% and most preferred, at least 80 vol.-% water. In the case of some analytes it can be additionally favorable to add to the aqueous sample further adjuvants, e.g. buffer for adjusting the pH, complexing agents or the like.

The solid phase used according to the invention is preferably washed at least once prior to use. Washing can be effected, for example, with water or buffer solution or buffer solution followed by dilute buffer or water.

Purification can be further improved by subjecting the solid phase separated in step (c), to the surface of which the proteinaceous material is bound, to at least one washing step. In this way impurities bound to the solid phase are separated off, however, not analyte bound to the solid phase. The composition of the washing solution is determined depending on the intended use and the surface, Preferably, a buffer solution is used selected from water, TFA (trifluor acetic acid), preferably 0.1% (v/v), acetic acid, preferably 5% (v/v) and 10–100 mmol/l Tris-HCl pH 7–9. Often it is also favorable to carry out several washing steps for purification with different washing buffers to eliminate different impurities.

In a further step, the analyte molecules bound to the surface can then be separated from the solid phase, preferably by means of an elution solution. As elution solution, any liquid can be used which again separates the proteinaceous material from the solid phase. The choice of the elution solution depends on the type of surface used and the analyte as well as on the subsequent use. Preferably, an organic solvent, especially acetonitrile, ethanol or isopropanol in a concentration of from 0–100 vol-%, especially from 30–80 vol.-%, is used for elution. The elution of proteins from hydrophobic surfaces is well-known to a skilled artisan and basically the same elution solvents as used in reversed phase column chromatographic purification of proteins and peptides can be employed here as well.

After separation of the analyte a magnetic solid phase again can be separated off by magnetic means, thus achieving complete automatization of the process of the invention.

The material isolated and/or purified according to the claimed process can be used directly for further analysis, e.g. mass spectrometric analysis. In that case manual purification via columns, which has been necessary so far, is no longer required. Rather is it possible to automatically purify and concentrate a large number of samples cost-efficiently and quickly for mass-spectrometric analysis, in particular, MALDI-MS analysis or ESI (eletrosprayionization)-MS analysis. The eluate thereby can be applied directly to the MALDI sample carrier. Other accompanying substances of the sample such as buffer substances, metal cations, nucleic acids, lipids, detergents etc. can be eliminated.

The process of the invention can be easily automated, with at least one and preferably all procedural steps being carried out automatically.

A further advantage is the large volume range to work in according to the process of the invention. Volumes ranging from ml to the upper nl range are possible, especially $\leq 10$ ml, preferably, $\leq 1$ ml and especially preferred $\leq 100 \mu$l and $\geq 100$ nl, preferably, $\geq 1 \mu$l. The volume range of the eluate can be adjusted to the respective application, with a concentrated sample being obtained in the case of a small elution volume.

The process of the invention is further illustrated by the following Example.

EXAMPLE 1

Aliquots of 50 $\mu$l of suspensions containing magnetic particles, $\beta$=2.5 mg/ml are washed and conditioned. For that purpose the particles are first immobilised in a 0.5 ml Eppendorf-reaction vessel onto the vessel wall using a strong magnet and the supernatant fluid was drawn up with a pipette. Subsequently, 50 $\mu$l 0.1% (v/v) TFA was added and the particles suspended. After a repeated magnetic separation the particles are washed with 50 $\mu$l 60% (v/v) acetonitrile in 0.1% TFA and again suspended in 50 $\mu$l 0.1% TFA. About 100 $\mu$l of a solution containing peptides to be purified is added to this suspension. After thoroughly mixing (e.g. by shaking) the fluid is removed from the particles being magnetically separated and substituted by 15 $\mu$l water. After repeated mixing and magnetic immobilising about 3–5 $\mu$l elution agent (e.g. 60% (v/v) acetonitrile in 0.1% TFA) are added. The eluted peptides can be directly analysed by mass-spectrometry or frozen and stored for later use.

What is claimed is:

1. A process for isolating a proteinaceous material in an aqueous sample comprising the steps:
   (a) providing an aqueous sample comprising a proteinaceous material,
   (b) contacting the aqueous sample with a solid phase having a surface on which is a mixture of hydrophobic groups and hydrophilic groups for binding the proteinaceous material to the solid phase, wherein the solid phase comprises magnetic solid particles having a diameter from $\geq 1$ nm to $\leq 10$ mm, and wherein the proteinaceous material is bound reversibly and nonspecifically to said hydrophobic groups,
   (c) removing unbound components from the solid phase,
   (d) releasing the bound proteinaceous material from the solid phase, and
   (e) removing the magnetic solid particles by magnetic separation, thereby isolating the proteinaceous material.

2. The process of claim 1, wherein the particles are paramagnetic or ferromagnetic.

3. The process according to claim 1, wherein the hydrophobic groups are alkyl groups or aryl groups.

4. The process according to claim 3, wherein the alkyl groups are at least one of a $C_8$ alkyl and a $C_{18}$ alkyl.

5. The process according to claim 1, wherein the hydrophilic groups are hydroxyl groups.

6. A process for isolating a proteinaceous material in an aqueous sample comprising the steps:

(a) providing an aqueous sample comprising a proteinaceous material, (b) contacting the aqueous sample with a solid phase having a surface on which is a mixture of hydrophobic groups and hydrophilic groups for binding the proteinaceous material to the solid phase, wherein the solid phase comprises magnetic solid particles having a diameter from $\geq 1$ nm to $\leq 10$mm, and wherein the proteinaceous material is bound reversibly and nonspecifically to said hydrophobic groups, (c) removing unbound components from the solid phase, (d) releasing the bound proteinaceous material from the solid phase, and (e) removing the magnetic solid particles by magnetic separation, thereby isolating the proteinaceous material, and wherein the molar ratio of hydrophobic to hydrophilic groups is from 10:1 to 1:10.

7. The process according to claim 1, wherein removing unbound components from the solid phase having proteinaceous material bound thereto comprises at least one washing step.

8. The process according to claim 1, wherein the isolated proteinaceous material is analyzed by mass spectrometry.

9. The process according to claim 1, wherein the magnetic separation is automated.

* * * * *